(12) United States Patent
Earnst et al.

(10) Patent No.: US 7,154,991 B2
(45) Date of Patent: Dec. 26, 2006

(54) PATIENT POSITIONING ASSEMBLY FOR THERAPEUTIC RADIATION SYSTEM

(75) Inventors: Eric Earnst, Saratoga, CA (US); Gopinath Kuduvalli, San Jose, CA (US); Vladimir Mitrovic, Foster City, CA (US); Matthew Core, Mountain View, CA (US)

(73) Assignee: Accuray, Inc., Sunnyvale, CA (US)

(*) Notice: Subject to any disclaimer, the term of this patent is extended or adjusted under 35 U.S.C. 154(b) by 139 days.

(21) Appl. No.: 10/687,860

(22) Filed: Oct. 17, 2003

(65) Prior Publication Data

US 2005/0085710 A1   Apr. 21, 2005

(51) Int. Cl.
*A61N 5/10* (2006.01)

(52) U.S. Cl. .......................... 378/65; 378/208

(58) Field of Classification Search ................. 378/65, 378/64, 205, 208–209
See application file for complete search history.

(56) References Cited

U.S. PATENT DOCUMENTS

| | | | |
|---|---|---|---|
| 2,295,006 A | 9/1942 | Philips | |
| 2,787,506 A | 4/1957 | Travisano | |
| 3,069,543 A | 12/1962 | Sazavsky | |
| 3,262,133 A | 7/1966 | Beitzel | |
| 3,640,520 A | 2/1972 | Wieland et al. | |
| 3,806,109 A | 4/1974 | Weber et al. | |
| 3,997,926 A | 12/1976 | England | |
| 4,259,756 A | 4/1981 | Pace | |
| 4,579,323 A | 4/1986 | Brendl et al. | |
| 4,603,845 A | 8/1986 | Schmedemann | |
| 4,618,133 A | 10/1986 | Siczek | |
| 4,672,697 A | 6/1987 | Schurch | |
| 4,697,802 A | 10/1987 | Brendl et al. | |
| 4,749,177 A | 6/1988 | Schafer et al. | |
| 4,841,585 A | 6/1989 | Masuzawa | |
| 4,872,657 A | 10/1989 | Lussi | |
| 5,022,810 A | 6/1991 | Sherrow et al. | |
| 5,207,223 A | 5/1993 | Adler | 128/653.1 |
| 5,299,334 A | 4/1994 | Gonzalez | |
| 5,345,632 A | 9/1994 | Langenaeken et al. | |
| 5,361,436 A | 11/1994 | Hahn | |
| 5,427,097 A | 6/1995 | Depp | |

(Continued)

OTHER PUBLICATIONS

Alejandro Mazal et al., "Robots in patient positioning for external radiotherapy", presentation, 46th American Association of Physicists in Medicine Annual Meeting, Pittsburgh, Jul. 2004.

(Continued)

*Primary Examiner*—David V. Bruce
*Assistant Examiner*—Hoon Song
(74) *Attorney, Agent, or Firm*—Blakely, Sokoloff, Taylor & Zafman LLP (57) ABSTRACT

A patient positioning assembly for therapeutic radiation treatment includes a support device for supporting the patient during treatment, and a controller for controlling the motion of the support device so that the treatment target within the patient is properly aligned with respect to a radiosurgical treatment apparatus throughout the treatment. The controller generates motion command signals for implementing corrective motions of the support device. The corrective motions align the target so that the position and orientation of the target, as shown in near real time image data, substantially match the position and orientation of the target, as shown in pre-treatment scans. One or more user interface modules, for example a handheld remote control module and a user interface screen, allows the user to interactively control the motion of the support device, by implementing one or more user selectable functions.

60 Claims, 4 Drawing Sheets

U.S. PATENT DOCUMENTS

| | | | |
|---|---|---|---|
| 5,499,415 A | 3/1996 | McKenna | |
| 5,572,569 A | 11/1996 | Benoit et al. | |
| 5,655,238 A | 8/1997 | Stickley et al. | |
| 5,790,996 A | 8/1998 | Narfstrom | |
| 5,820,553 A * | 10/1998 | Hughes | 378/65 |
| 5,825,843 A | 10/1998 | Kobayashi | |
| 5,983,424 A | 11/1999 | Naslund | |
| 6,125,164 A * | 9/2000 | Murphy et al. | 378/65 |
| 6,138,302 A | 10/2000 | Sashin et al. | 5/600 |
| 6,279,579 B1 | 8/2001 | Riaziat et al. | 128/897 |
| 6,385,286 B1 * | 5/2002 | Fitchard et al. | 378/65 |
| 6,484,332 B1 | 11/2002 | Korver, II et al. | |
| 6,501,981 B1 | 12/2002 | Schweikard et al. | |
| 6,516,046 B1 | 2/2003 | Frohlich et al. | 378/65 |
| 6,810,108 B1 * | 10/2004 | Clark et al. | 378/65 |
| 6,865,253 B1 * | 3/2005 | Blumhofer et al. | 378/65 |

OTHER PUBLICATIONS

"Adept Technology Announces Extension of SmartServo Architecture to SCARA Robots", Adept Technology, Inc., News Article, Sep. 18, 2002, 2 pages.

"Adept Technology Introduces Four New SCARA Robots with Adept's SmartServo Architecture", Adept Technology, Inc.—News Article, Apr. 14, 2003, 2 pages.

"EC Series SCARA Robots", Seiko EC SCARA Robots, 2003, Epson America, Inc., 3 pages, downloaded Nov. 18, 2004, http://www.seikorobots.com/products/ecrbts.htm.

"EH Series SCARA Robots", Epson EH SCARA Robots, 2 pages, downloaded Nov. 18, 2004, http://www.robots.epson.com/products/ehrbts.htm.

"SCARA Robot—Adept Cobra s600", SCARA Robot—Adept Cobra s600—tabletop factory automation, 2 pages, downloaded Nov. 18, 2004, http://www.adept.com/main/products/robots/cobra_s600.shtml, 2 pages.

Adept Cobra s600 Robot with CS or CX (90565-00x), Adept Technology, Inc., Nov. 5, 2004, 5 pages.

"Adept SmartCartesian™", Adept Technology, Inc., Mar. 26, 2002, 1 page.

"HS & HM Series SCARA Robots", Motoman, Solutions in Motion, 4 pages, 2002 Motoman, Inc. Sep. 2002.

"EPH4000" Motoman, Solutions in Motion, 2 pages, 2004 Motoman, Inc., Feb. 2004.

"AdeptXL SCARA Robots", downloaded Nov. 30, 2004, http://www.adept.com/main/products/robots/AdeptXL.shtml, 1 page.

"AdeptThree XL SCARA Robot", 2000-2004, Adept Technology, Inc., downloaded Nov. 30, 2004, http://www.adept.com/main/products/robots/AdeptThree.shtml, 1 page.

Pro Six (6-Axis), Epson Pro Six 6-Axis Robots (also called Vertical Articulated robots), 3 pages, downloaded Nov. 30, 2004, http://www.robots.epson.com/products/prosixrbts.htm.

"E2H SCARA Robots", Epson E2H SCARA Robots, downloaded Nov. 30, 2004, http://www.robots.epson.com/products/e2hrbts.htm, 3 pages.

"UP6" Payload: 6 kg, Motoman, Solutions in Motion, 2 pages., 2003 Motoman Inc., Oct. 2003.

"UP20MN" Payload: 20 kg, Motoman, Solutions in Motion, 2 pages, 2004 Motoman Inc., Mar. 2004.

"HP20" Payload: 20 kg, Motoman, Solutions in Motion, 2 pages, 2004 Motoman Inc., Apr. 2004.

"Motoman-CR50", Type: YR-CR50-A00, 1 page, http://www.motoman.com/products/robots/default.htm, 2001-2005, Motoman Inc., downloaded May 12, 2005.

"Welding One Step Ahead, Linear Units", Kuka Robot Group, downloaded Apr. 20, 2005, http://www.kuka.com/en/products/addons/linearunits/start.htm, 1 page.

"KR6", Kuka Robot Group, downloaded Nov. 17, 2004, http://www.kuka.com/en/products/robots/low/kr6/start.htm, 1 page.

"KR16", Kuka Robot Group, downloaded Nov. 17, 2004, http://www.kuka.com/en/products/robots/low/kr16/start.htm, 1 page.

"KR 16 KS" Kuka Robot Group, downloaded Nov. 17, 2004, http://www.kuka.com/en/products/robots/low/kr16_ks/start.htm, 1 page.

"KR 16 L6", Kuka Robot Group, downloaded Nov. 17, 2004, http://www.kuka.com/en/products/robots/low/kr16_16/start.htm, 1 page.

"KR 30-3", Kuka Robot Group, downloaded Nov. 17, 2004, http://www.kuka.com/en/products/robots/medium/kr30_3/start.htm, 1 page.

"KR 30-3 KS", Kuka Robot Group, downloaded Nov. 17, 2004, http://www.kuka.com/en/products/robots/medium/kr30_3_ks/start.htm, 1 page.

KR 30 HA (High Accuracy), Kuka Robot Group, downloaded Nov. 17, 2004, http://www.kuka.com/en/products/robots/medium/kr30_ha/start.htm, 1 page.

"KR 60-3", Kuka Robot Group, downloaded Nov. 17, 2004, http://www.kuka.com/en/products/robots/medium/kr60_3/start.htm, 1 page.

"KR 60-3 KS", Kuka Robot Group, downloaded Nov. 17, 2004, http://www.kuka.com/en/products/robots/medium/kr60_3_ks/start.htm, 1 page.

KR 100 P (Series 2000), Kuka Robot Group, downloaded Nov. 17, 2004, http://www.kuka.com/en/products/robots/high/kr100_p_2000/start.htm, 1 page.

KR 150 K (Series 2000), Kuka Robot Group, downloaded Nov. 17, 2004, http://www.kuka.com/en/products/robots/high/kr150_k_2000/start.htm, 1 page.

"KR 500 570 PA/1", Kuka Robot Group, downloaded Nov. 17, 2004, http://www.kuka.com/en/products/robots/heavy/kr500_570_pa/start.htm, 1 page.

"Linear Units", Kuka Robot Group, downloaded Nov. 30, 2004, http://www.kuka.com/cgi-bin/MsmGo.exe?grab_id=11&page_id=9375232&query=Linear+Units&hiword=LINEAREN+LINEARLY+Linear+UNIT+UNITE+UNITED+Units+, 1 page.

"KR 500 570 PA/1", Kuka Robot Group, downloaded Nov. 30, 2004, http://www.kuka.com/en/products/robots/heavy/kr500_570_pa/start.htm, 1 page.

"iThemba LABS Medical Radiation Group, New Treatment Station, Non-Orthogonal Beam Lines for Proton Therapy", Seite 1 von 2, downloaded Aug. 3, 2004, http://www.medrad.nac.ac.za/npther.htm, 12 pages.

KR 210-2 (Series 2000), Kuka Robots USA, downloaded Jan. 21, 2005, http://www.kuka.com/usa/en/products/robots/high/kr210_2_2000/start.htm, 1 page.

KR360/1, KR360 450 PA/1, KR 360 L150 P/1, KR 500/1, KR 500 570 PA/1, Mar. 1, 2005, cover sheet and pp. 13-22, 33-58.

"CyberKnife", Stereotactic Radiosurgery System using image-guided robotics, downloaded Nov. 16, 2004, http://www.accuray.com/ck/deliv18.htm, 3 pages.

E.A. de Kock et al., "Integrating an industrial robot and multi-camera computer vision systems into a patient positioning system for high-precision radiotherapy", Wednesday, Mar. 24, 2004, 6 pages, ISR 2004 Symposium, Mar. 23-26, 2004.

Linac Scalpel, "RadioCameras™ System, Frameless Stereotactic Radiotherapy and Radiosurgery," Zmed Inc., 2001.

TomoTherapy Incorporated, "The Tomo® Advantage: TomoImage™", 2003.

TomoTherapy Incorporated, "A True Integrated Treatment System", 2003.

BrainLAB Radiotherapy Solutions, "A good idea perfected, ExacTRAC$^{xray60}$, BrainLAB's unique X-Ray based targeting technology. Available as an upgrade to your existing Linac", 2003 BrainLAB AG.

Neurosurgery News, New Products/Press Releases, "Elekta Receives FDA Clearance for Elekta Synergy™, New radiotherapy system from Elekta combines x-ray volume imaging and treatment in a single platform", Fall 2003, pp. 17-18.

North American Scientific, NOMOS Radiation Oncology Division, "IMRT/IMRS Delivery System", 2003.

Varian Medical Systems, Oncology Systems, Treatment Delivery, Exact Couch™ Couch and Indexed Immobilization™, 1999-2005 Varian Medical Systems, Inc.

Milton K. Woo, Bryan Kim, "An investigation of the reproducibility and usefulness of automatic couch motion in complex radiation therapy techniques", Journal of Applied Clinical Medical Physics, vol. 3, No. 1, Winter 2002, pp. 46-50.

Linear Accelerators (5 pages), Sep./Oct. 2003, from Imaging Technology News, Sep./Oct. 2003, vol. 43, No. 5, www.ITNonline.net, + Cover page, Table of Contents (2 pages), 7 pages total.

"International Search Report", International Searching Authority, PCT/US04/28011, Oct. 31, 2005, 2 pgs.

"Written Opinion of the International Searching Authority", International Searching Authority, PCT/US04/28011, Oct. 31, 2005, 5 pgs.

* cited by examiner

PATIENT POSITIONING ASSEMBLY FOR THERAPEUTIC RADIATION SYSTEM

FIELD OF THE INVENTION

The present invention relates to a patient positioning assembly for therapeutic radiation systems.

BACKGROUND

The term radiosurgery refers to a procedure in which intense and precisely directed doses of radiation are delivered to a target region in a patient, in order to destroy tumorous cells or otherwise treat the target region. The term radiotherapy refers to a procedure in which radiation is applied to a target region for therapeutic, rather than necrotic, purposes. The amount of radiation utilized in radiotherapy is typically about an order of magnitude smaller, as compared to the amount used in radiosurgery. Radiotherapy is frequently used to treat early stage, curable cancers. For convenience, the term "radiosurgery" in this application shall henceforth mean "radiosurgery and/or radiotherapy."

In radiosurgery, it is necessary to determine with precision the location of the target region (and surrounding critical structures) relative to the reference frame of the treatment device. It is also necessary to control the position of the radiation source so that its beam can be precisely directed to the target tissue while avoiding surrounding healthy tissue, with control of propagation in and through other body structures.

To effect such beam position control, a frameless stereotactic radiosurgery system has been developed, which implements image-guided radiosurgery using a robot. An image-guided robotic system provides the requisite beam position control for accurate delivery of therapeutic radiation, while eliminating the need for rigid stereotactic frames. Such image-guided robotic systems typically include a treatment beam generator, for example an x-ray source, mounted onto a robot, and a controller. The x-ray source provides precisely shaped and timed radiation beams. Using pre-treatment scan data, as well as treatment planning and delivery software, the controller acquires information regarding the pre-treatment position and orientation of the treatment target region. The patient is usually placed on a support device, such as a couch or a table. During treatment, an imaging system repeatedly measures the position and orientation of the target relative to the x-ray source. Prior to the delivery of radiation at each delivery site, the controller directs the robot to adjust the position and orientation of the x-ray source, in accordance with the measurements made by imaging system, so that the requisite dose of the treatment beam can be applied to the treatment target within the patient.

While operating these image-guided robotic systems, it is necessary to adjust the position and orientation of the patient in order to ensure that the target within the patient remains properly aligned with respect to the treatment beam. The position and orientation of the patient must be corrected, for example, in order to compensate for any motion (such as respiratory motion, sneezing, or shifting) that the patient may undergo during treatment.

Accordingly, it is desirable to provide a patient positioning assembly that includes a dynamic motion control mechanism for controlling the motion of the support device, so that the position and orientation of the support device can be adjusted as necessary.

SUMMARY OF THE INVENTION

A patient positioning assembly is provided for adjusting patient position during therapeutic radiation treatment using a radiosurgery apparatus. The radiosurgery apparatus includes a robot having an articulated arm assembly; an x-ray source mounted at one end of the arm assembly; an imaging system; a support device for supporting the patient during treatment, and a controller for controlling the motion of the support device. The controller receives pre-treatment scan data representative of one or more pre-treatment scans of a treatment target within the patient. The pre-treatment scans show the position and orientation of the target with respect to a pre-treatment coordinate system. The controller receives image data representative of near real time images of the target. The image data contain information regarding the near real time position and orientation of the target with respect to a treatment coordinate system. The treatment coordinate system and the pre-treatment coordinate system are related by known transformation parameters.

The controller generates motion command signals for implementing corrective motions of the support device for aligning the target with respect to the radiation treatment beam, so that the position and orientation of the target, as shown in the near real-time image data, substantially match the position and orientation of the target as shown in the pre-treatment scan data of the target. In one embodiment, the corrective motions of the support device are relative to the robot-implemented motions of the x-ray source. In this embodiment, the robot-implemented movements of the x-ray source are complemented by the corrective motions of the support device, so that the relative motion between the x-ray source and the support device ensures the delivery of the desired radiation pattern throughout the target region.

In one embodiment, the corrective motions of the support device are coordinated with the motions of the x-ray source, in a way as to maximize the workspace available to the radiosurgery apparatus. In another embodiment, the corrective motions of the support device accommodate for various patient motions, such as breathing, coughing, sneezing, hiccuping, heartbeat, and muscular shifting.

The controller includes at least one user interface unit for enabling the user to interactively control the corrective motions of the support device, by implementing one or more user-selectable functions.

DETAILED DESCRIPTION

A patient positioning assembly is provided for adjusting patient position and orientation during therapeutic radiation treatment. In one embodiment, the patient positioning assembly is used with a frameless, image-guided radiosurgery system, such as the Cyberknife system developed by Accuray, Inc., although in other embodiments the patient positioning assembly can be used with other types of therapeutic radiation systems.

Figure 1:
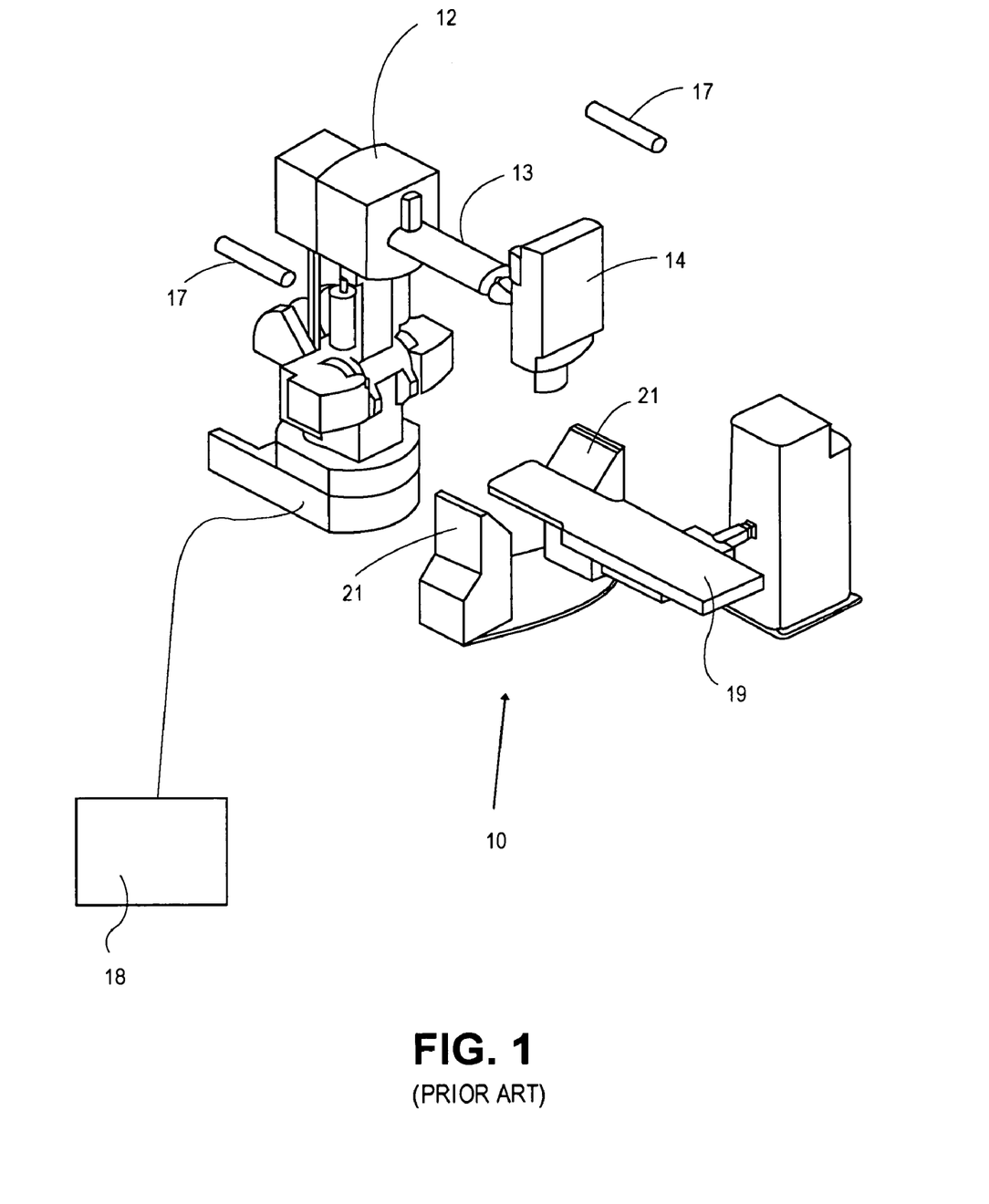
FIG. 1 schematically illustrates the Cyberknife frameless radiosurgery system, known in the prior art.

FIG. 1 schematically illustrates the Cyberknife radiosurgery system 10, known in the art. In overview, the radiosurgery system 10 includes: a robot 12, having an articulated arm assembly 13; a therapeutic radiation source 14, mounted at a distal end of the articulated arm assembly 13, for selectively emitting therapeutic radiation; an x-ray imaging system; and a controller 18. In the illustrated embodiment, the therapeutic radiation source 14 is an x-ray linear accelerator ("linac"). The x-ray imaging system generates image data representative of one or more near real time images of the target. The x-ray imaging system includes a pair of diagnostic x-ray sources 17, and a pair of x-ray image detectors (or cameras) 21, each detector located opposite an associated one of the x-ray sources 17. A patient support device (or treatment table) 19 supports the patient during treatment, and is positioned between the two x-ray cameras 21 and their respective diagnostic x-ray sources 17.

The imaging system generates, in near real time, x-ray images showing the position and orientation of the target in a treatment coordinate frame. The controller 18 contains treatment planning and delivery software, which is responsive to pre-treatment scan data CT (and/or MRI data and/or PET data and/or ultrasound scan data) and user input, to generate a treatment plan consisting of a succession of desired beam paths, each having an associated dose rate and duration at each of a fixed set of nodes. In response to the controller's directions, the robot 12 moves and orients the x-ray linac 14, successively and sequentially through each of the nodes, while the x-ray linac 14 delivers the required dose as directed by the controller 18. The pre-treatment scan data may include, for example, CT scan data, MRI scan data, PET scan data, and ultrasound scan data.

Prior to performing a treatment on a patient with the CyberKnife, the patient's position and orientation within the frame of reference established by the CyberKnife's x-ray imaging system 16 must be adjusted to match the position and orientation that the patient had within the frame of reference of the CT (or MRI or PET) scanner that provided the images used for planning the treatment. It is desirable that this alignment be performed to within tenths of a millimeter and tenths of a degree for all six degrees of freedom.

Figure 2:
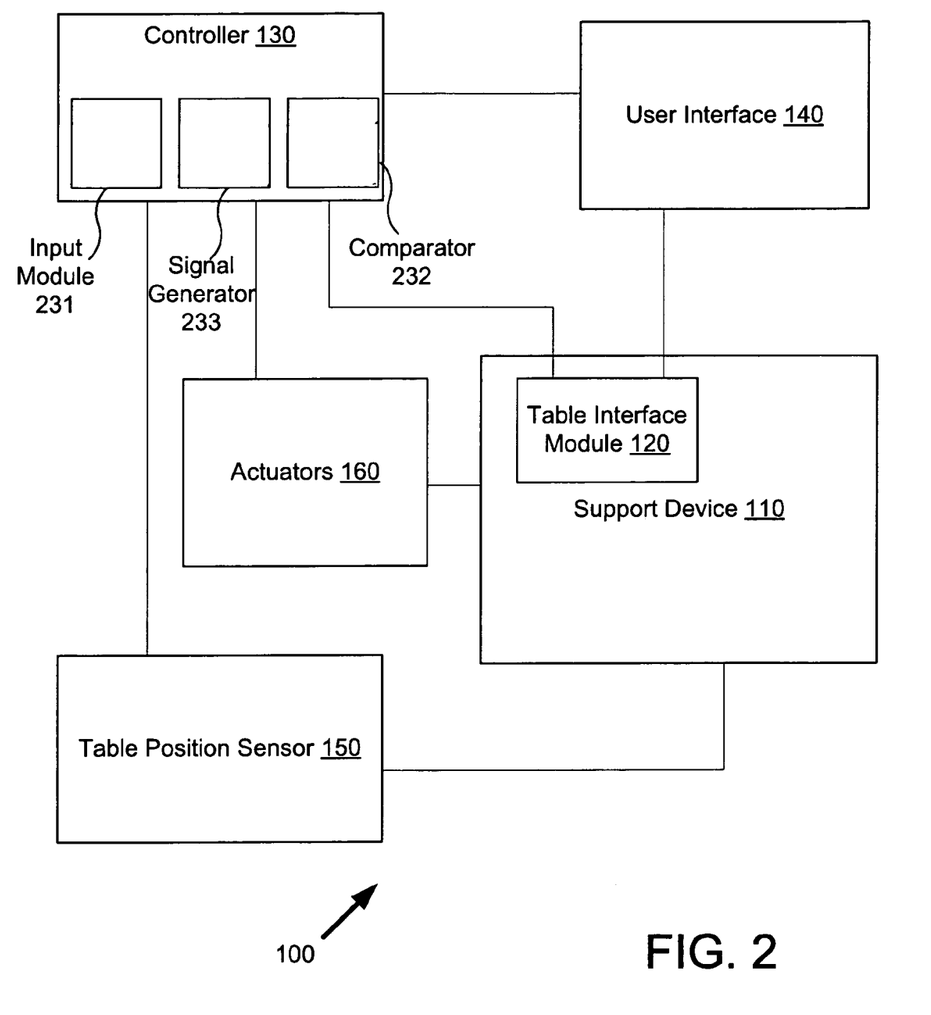
FIG. 2 is a schematic block diagram of a patient positioning assembly for therapeutic radiation treatment.

FIG. 2 provides a schematic block diagram of a patient positioning assembly 100 that adjusts patient position under computer control, during radiosurgery. In the illustrated embodiment, the patient positioning assembly 100 is adapted for use in conjunction with the Cyberknife robotic image-guided radiosurgery system, illustrated in FIG. 1. In overview, the patient positioning assembly 100 includes: 1) a support device 110 for supporting the patient during treatment; 2) a controller 130 for controlling the motion of the support device 110 in a way that the treatment target within the patient's anatomy remains properly aligned with respect to the treatment beam source throughout the treatment procedure.

One or more table position sensors 150 are provided to sense the position of the table 110. One or more table motion actuators 160 are provided for moving the table, in accordance with directions from the controller 130. A table interface module 120 allows the table to interface with the sensors 150, the actuators 160, the controller 130, and the user interface 140. In the illustrated embodiment, the table interface module 120 is an electronics module embedded within the table. The table interface module 120 manages communications between the table 110, and the user interface 140 and the controller 130, accepting motion commands and providing position feedback and other status messages. The electronics module 120 can independently check table positions against a model of surrounding obstructions to ensure that the table doesn't collide with any obstacles during table motion. The module 120 could be a retrofit item or be a functionality designed as part of the table's original design requirements.

In one embodiment, the patient positioning assembly 100 further includes at least one user interface 140, including one or more user interface units that enables a user or operator to interactively participate in controlling the motion of the support device.

In the illustrated embodiment, the support device 110 is a treatment table, although in other embodiments other types of support devices (such as a chair or bench) may be used. A communications link (not illustrated) between the controller 130 and the table 110 enables communications between the table 110 and the controller 130. The communications link can be a wired link or a wireless link, with a bandwidth necessary for maintaining reliable and timely communications.

One or more table position sensors 150 are provided to sense the position of the table 110. One or more table motion actuators 160 are provided for moving the table, in accordance with directions from the controller 130. A table interface module 120 allows the table to interface with the sensors 150, the actuators 160, the controller 130, and the user interface 140. In the illustrated embodiment, the table interface module 120 is an electronics module embedded within the table. The table interface module 120 manages communications between the table 100, and the user interface 140 and the controller 130, accepting motion commands and providing position feedback and other status messages. The electronics module 120 can independently check table positions against a model of surrounding obstructions to ensure that the table doesn't collide with any obstacles during table motion. The module 120 could be a retrofit item or be a functionality designed as part of the table's original design requirements.

The controller 130 includes an input module 231 for receiving 1) pre-treatment scan data representative of pre-treatment scans of the target, and 2) near real time image data representative of near real time images of the target. The pre-treatment scans show the position and orientation of the target with respect to the pre-treatment coordinate system. The near real-time images, taken by the imaging system under the command of the controller, show the position and orientation of the target with respect to the treatment coordinate system. The treatment coordinate system and the pre-treatment coordinate systems are related by known transformation parameters. The controller includes a TLS (target location system) processing unit that computes the position and orientation of the target in the treatment coordinate system, using the pre-treatment scan data, the near real time image data, and the transformation parameters between the pre-treatment coordinate system and the treatment coordinate system.

The controller 130 includes a comparator 232, or other software for comparing the position and orientation of the target, as shown in the near real-time image data, with the position and orientation of the target as shown in the pre-treatment scan data. The controller computes the amount of translations (in three degrees of freedom) and rotations (in three degrees of freedom) that are required in order for the position and orientation of the target, as shown in the near real time images, to substantially match the position and orientation of the target, as shown in the pre-treatment scans. The controller 130 includes software for converting this information into one or more units of motion of the table, in at least three degrees of freedom, and preferably in five or six degrees of freedom. The controller 130 includes a signal generator 233, or other software for generating at least one motion command signal for implementing corrective motions of the table, which align the treatment target within the patient with respect to the radiosurgery system in such a way that the position and orientation of the target, as shown in the near real time images generated by the imaging system, substantially match the position and orientation of the target as shown in the pre-treatment scans.

In one embodiment, the controller 130 controls the motion of the x-ray source 14, as well as the motion of the table 110. In other words, the controller 130 controls the relative motion of the table 110, with respect to the robot-implemented motion of the x-ray source 14. In this way, the corrective motions of the table, implemented by the motion command signal from the controller 130, compensates for one or more motions of the x-ray source implemented by the robot.

This feature is useful, for instance, when there are practical limits on where the robot can place the x-ray source, and how the robot can implement the requisite movements of the x-ray linac, in order to deliver a desired radiation pattern to the target. There may be restrictions on where the x-ray source can move to, because of the configuration of the radiosurgery system. In such cases, the patient positioning assembly 100 is capable of dynamically controlling the motion of the support device 110, so as to implement any trade-off motions that are necessary for correctly aligning the patient relative to the treatment beam, and for delivering the correct radiation pattern to the target. In one embodiment, the combination of the motions of the table 110 and the motions of the x-ray linac 14, are dynamically coordinated and controlled, so as to maximize the workspace available to the radiosurgery system.

In one embodiment, the corrective motions of the table 110, implemented by the motion command signals generated by the controller 130, compensate for various patient motions that the patient may undergo, during treatment. These patient motions may include, but are not limited to, the following: respiratory motion; cardiac pumping motion of the patient's heart; sneezing, coughing, or hiccuping; and muscular shifting of one or more anatomical members of the patient.

The table 110 is capable of motion in at least three degrees of freedom, namely three translational degrees of freedom (x-, y-, and z-). Preferably, the table is capable of motion in all six degrees of freedom, namely three translational degrees of freedom plus three rotational degrees of freedom (roll-, pitch-, and yaw-rotations). The motion command signal, generated by the controller, thus controls corrective motions of the table in at least three, and preferably five or six, degrees of freedom.

In one embodiment, the table 110 is capable of motion in five degrees of freedom (three translational, plus roll- and pitch-rotations), and an external device such as a robot is used for correcting for yaw-rotations. In this embodiment (not illustrated), the controller includes software for performing a number of functionalities for correcting yaw rotation, using the robot. These functionalities include TLS functionality to verify if any workspace (reachability, patient proximity, or image blocking) errors are encountered when attempting to correct for yaw over the maximum range of yaw to be corrected. The software zeroes out any node for which the yaw correction can lead to a workspace error. Also included is robot functionality to utilize the rotations reported by the target locating system and to correct for them.

The software includes a functionality for standardizing the robot motion from node to node by moving with no corrections, such that robot motion errors are minimized during treatment delivery. The correction of yaw error can be extended to the other two rotations, roll and pitch, with greater reduction in workspace. In one embodiment, the external device (robot) may correct for any of the 5 degrees of freedom, as well as for the sixth degree of freedom.

The controller 130 includes software for establishing and maintaining a reliable communication interface with the table over a bus interface, for example the Ethernet-to-Serial-to-CAN (Controller Area Network) bus interface. The software uses the interface specifications developed for the table 110. The controller 130 further includes software for converting the patient position and orientation information from the imaging system to appropriate units of movement in the 5 degrees of freedom of motion capability of the table. The algorithms are scalable to use all 6 degrees of freedom. The controller further includes software for providing a user interface to on the CyberKnife user control console, to inspect and initiate the table motion to position the patient. The controller further includes software for detecting, reporting and handling errors in communication or software control of the table.

The user interface 140 effects computer control of the three, five or six degrees of freedom of the table 110. In a particular embodiment, the user interface 140 includes: a bus interface for connecting the table to the Cyberknife primary workstation; at least one user interface unit for allowing the user to interface with the controller to interactively control the table motion; and a hardware interface to the Cyberknife E-stop (emergency stop) circuitry. The bus interface may be a CAN bus interface that can be connected to the Cyberknife primary workstation using Ethernet-to-Serial-to-CAN bus converters. The user interface unit can be a secondary unit on such a CAN bus. The hardware interface to the E-stop circuitry disables to computer-controlled table motions when any E-stop is engaged.

The E-stop mechanism is operable to stop computer-controlled motion of the table 140. In one embodiment, the "System E-stop" is an emergency lockout mechanism, capable of shutting down any and all radiation, and any and all motion. In other words, the "System E-stop" shuts down at least the following: 1) generation of therapeutic x-ray beams by the x-ray source; 2) any motion of the x-ray source and/or the robot; 3) any motion of the table; and 4) the imaging system.

The user interface allows the user or operator to interactively participate in controlling the motion of the table, by implementing one or more user-selectable functions. These user-selectable functions include, but are not limited to, the following: 1) a function that allows the user to activate the x-ray imaging system, so that the acquisition of near real time images of the target can be initiated; 2) a function for allowing the user to move the table to a pre-programmed "HOME" position, which corresponds to a mounting position that facilitates the mounting of the patient onto the table; 3) a function for allowing the user to move the table to a pre-programmed "TREAT" position, which is the default treatment position; 4) a function for displaying to the user the three translations and two rotations corresponding to the table corrective motions needed to adjust the target position, in accordance with the information from the near real time images; 5) a function for allowing the user to compare the translations and rotations with respective pre-specified limits for each translation and rotation; 6) a function for allowing the user to modify one or more of the pre-specified limits; and 7) a function for allowing the user to verify that the translations and rotations fall below the pre-specified limits, and thereupon activate the x-ray source to initiate treatment delivery.

Figure 3:
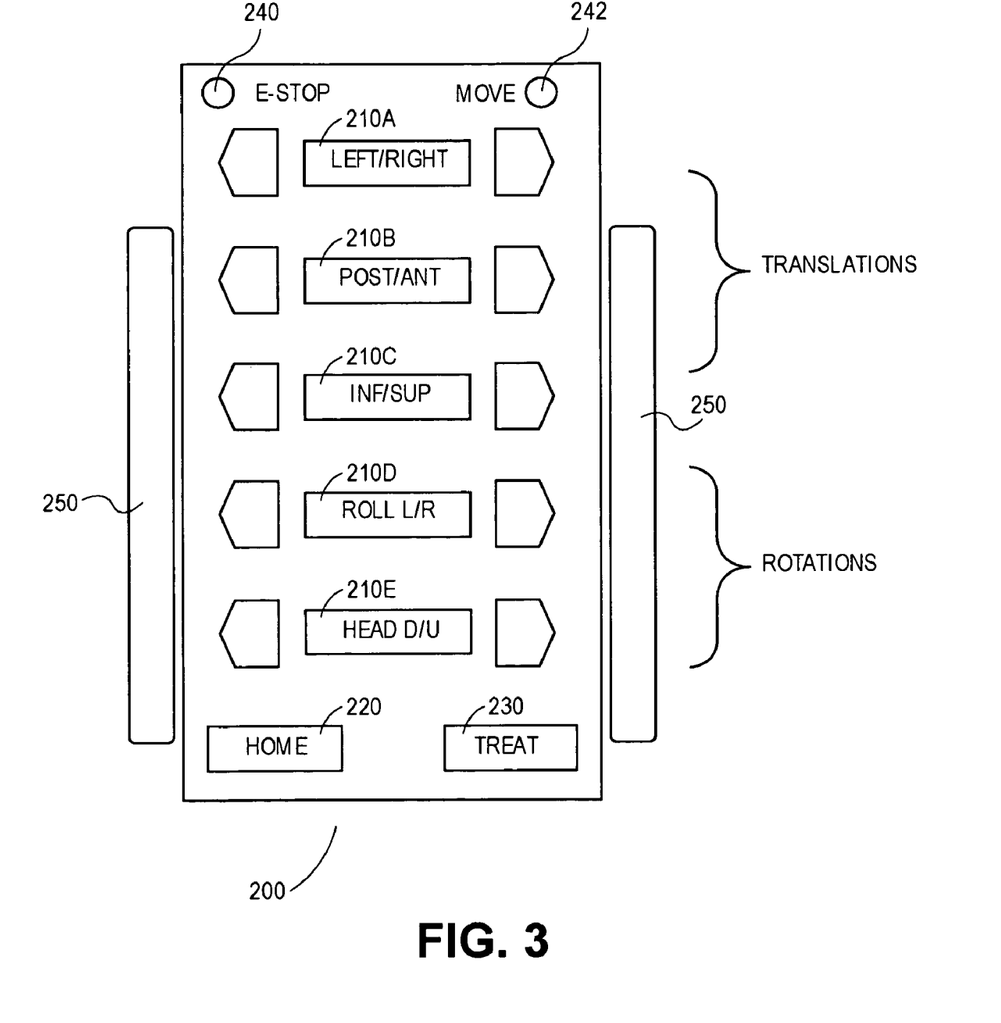
FIG. 3 is a schematic diagram of a handheld user interface unit, with remote control capabilities.

In a particular embodiment, the user interface unit is a remote control unit that provides a user with remote control capabilities for remote control of the motion of the support device 110. FIG. 3 is a schematic diagram of a handheld user interface unit 200, with remote control capabilities. In the illustrated embodiment, the user interface unit 200 is a handheld pendant, and includes a number of button icons respectively associated with these user-selectable functions. The handheld remote control unit 200 provides controls to manually adjust the patient's position, and status indicators related to the table motions.

In the illustrated embodiment, the handheld remote control unit 200 includes seven motion switches: five sets of axes motion control switches 210A–210E, a home switch 220, and a treat switch 230. The axes motion control switches provide bidirectional manual control of each degree of freedom via a pushbutton. The axes motion control switches cause movement of the desired axes (three translational axes: left/right (210A), posterior/anterior (210B), inferior (towards the feet)/superior (towards the head) (210C); 2 rotational axes: roll left/right (210D); head down/up (210E)) in the desired direction, as long as the switch is held down and motion is disabled. The home switch 220 initiates a programmed motion, if motion is enabled, that causes the table to automatically move to the fully retracted, fully lowered, and centered position without any further operator action. The treat switch 230 initiates a programmed motion, if motion is enabled, that causes the table to move to a position defined by the treatment computer and previously downloaded to the table.

The remote control unit 200 also includes a pair of status indicators 240 and 242, which are LEDs (light emitting diodes) that provide an indication of whether motions are enabled and being accepted. In the illustrated embodiment, the E-stop LED 240 is yellow when System E-stop is asserted, green when overridden by bypass switches, and off when no System E-stop is asserted. The MOVE LED 242 is green whenever a switch is pushed and motion is enabled, flashing green when a programmed movement is occurring, and yellow when the table E-stop is engaged.

The remote control unit 200 also includes a pair of motion enable switches 250. Depressing both switches enables all motion switches (axes motion control, home and treat), and overrides the System E-stop, if present, although it does not override table E-stop switches. Releasing one or both of the switches while a programmed motion is occurring will cause that motion to stop.

The remote control unit 200 may also include a Goto switch (not shown), allowing the user to access stored locations. The remote control unit 200 may also include display capabilities (not shown), for example to display to the user the three translations and two rotations, or to display informational messages to the user. The remote control unit 200 may also include absolute and relative position display/input modes (not shown).

Figure 4:
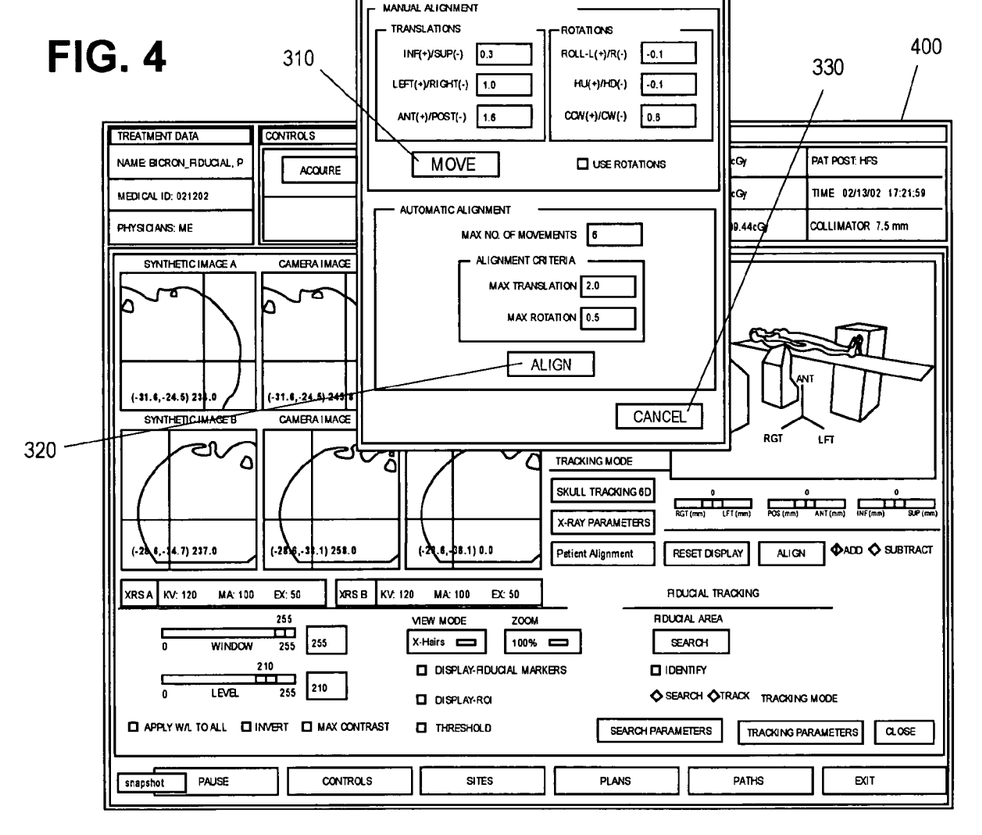
FIG. 4 illustrates an exemplary user interface screen, launched onto a treatment delivery display screen.

One or more user interface screens on the user control console of the primary Cyberknife workstation, allows the user to inspect, initiate, and interactively control the table motion to position the patient. FIG. 4 illustrates an exemplary user interface screen 300, launched into a treatment delivery screen 400 of the primary workstation. In the illustrated embodiment, the user interface screen 300 provides to the user an integrated table position display, and table motion control capabilities. The user interface screen 300 provides sub-options to adjust translations only, or rotations only or all the degrees of freedom available together.

In the illustrated embodiment, an ALIGN COUCH button in the treatment delivery screen 400 launches the user interface screen 300. The user interface screen 300 includes a number of fields, with different functions. These fields include translation and rotation fields, which are initially filled with the table corrective motions returned by the TLS unit of the controller. If no valid table corrective motions are available, these fields are left blank. The translation and rotation fields are editable.

In the illustrated embodiment, the user interface screen 300 includes a MOVE button 310, an "AUTO ALIGN" button 320, and a "CANCEL" button 330. The "MOVE" button 310 moves the table by the amount of translations and rotations indicated. If the "Apply rotation" field is unchecked, the table is moved only in translational units. The "AUTO ALIGN" button 320 initially moves the table by the amount of translations and rotations indicated, and proceeds to acquire images and correct table positions automatically until pre-specified "Auto align limits" are satisfied. This means that the translations and rotations are below the pre-specified limits, or the number of images indicated are taken. The "Auto align limits" fields are filled in from a system configuration file, but can be edited. The "CANCEL" button 330 will return to the Patient Alignment interface.

In one embodiment, the user interface screen 300 includes button icons that allow the user to adjust imaging parameters, such as the intensity, energy, and spectral distribution of the x-rays in the imaging beams generated by the imaging system; the number of near real time images to be acquired; the selection and de-selection of fiducials; and rigid body parameters.

In operation, an approximate treatment location for the patient is computed, as part of the treatment planning process. When the treatment plan is loaded into the controller, the approximate treatment location is downloaded into the treatment table. The operator positions the patient on the table, and applies any restraining devices. The operator then presses the "Treat" button in the handheld user interface unit 200 (shown in FIG. 3), and the table automatically moves to bring all of its degrees of freedom to the stored positions. Alternatively, the "Treat" command could also be issued from the computer interface screen. The number of axes to move simultaneously may be limited by design to ensure that power demands are not excessive and that the patient is comfortable with the number of simultaneous motions taking place.

The operator then exits the treatment room and using the user interface screen 300 (shown in FIG. 4) on the workstation or dedicated control panel, commands the system to align the patient to within desired tolerances. The user interface screen allows the user to enter parameters such as the maximum number of near real time images to take during the alignment process, and the desired tolerances for position and orientation. The user interface screen also allows the errors associated with each image to be displayed.

After obtaining a satisfactory alignment, the radiosurgery system is commanded to begin treatment. As part of the treatment, near real time images are obtained periodically by the imaging system, to ensure that the patient doesn't move during the treatment. If the patient does move, the operator can cause treatment delivery to be paused, and the patient to be realigned, by effecting appropriate corrective motions of the table. At the conclusion of the treatment, the operator reenters the treatment room and uses the "Home" button on the handheld user interface unit to return the table to the position for patient unloading. Alternatively, the system could issue the Home command from the computer screen.

Following is a more detailed description of the operation of the patient positioning assembly described above. During the initial treatment planning phase, the treatment planning system checks for the workspace-related issues that result from the attempt to correct for the patient yaw over the adjustable range. The adjustable range of yaw is specified in a data file. Any radiation nodes that encounter a workspace-related issue as a result of attempting to correct patient yaw over the adjustable range have the dose set to zero.

The next stage is the initial patient set-up stage. During this stage, the treatment planning files are downloaded, prior to patient entry into the treatment room. During the download of treatment files, the treatment position of the table is downloaded into the controller and then to the table interface module. The treatment position of the table is one of: a) a default table position for the beam path set selected; and b) a treatment position for the patient, the last time the same plan was used. Before the patient walks into the treatment room, the "HOME" button on the handheld remote control unit is pressed, so as to position the table in a pre-defined comfortable position for the patient to get onto the table. The patient is then immobilized, for example using aqua masks and or other immobilization devices.

The "TREAT" key on the handheld remote control unit is used to position the table to the nominal treatment position. For head treatments, or if this is a second or subsequent treatments for the patient with the same plan, the nominal treatment position is adequate for further automatic positioning, and the operator can proceed to the user control console for automatic positioning of the patient. Otherwise, the table is further manually adjusted, using the handheld remote control unit, so that the anatomical target region of interest is within the imaging field of view. The operator then proceeds to the user control console, for automatic positioning of the patient.

The next stage is the initial image acquisition stage. During this stage, the operator acquires images, using the ACQUIRE button on the patient alignment screen in the user interface screen 300 (shown in FIG. 4). If necessary, imaging parameters may need to be adjusted. Some examples of these parameters are: x-ray parameters; de-selection of fiducials that may have migrated or otherwise difficult to track; and adjustment of rigid body parameters.

The next stage is the one-time table alignment stage. The user selects the "AUTO COUCH" button on the patient alignment screen. This brings up a Couch Adjustment interface screen, which contains the initial corrections obtained from the TLS unit of the controller. The initial corrections from TLS are editable. The "MOVE" button moves the table by the amount of corrections indicated in the window. The option to disable rotation corrections are available. The "AUTO ALIGN" button perform the first correction, and proceeds to complete the automatic alignment.

The next stage is the automatic table alignment stage. The "AUTO ALIGN" button in the Couch Adjustment interface screen performs the automatic alignment. Auto Align starts by making the initial correction in the Couch Adjustment interface, and proceeds to take additional images and perform the correction from the image, until one of the following conditions are met: the desired number of images in the Auto Alignment phase are acquired, and/or the residual corrections fall below the limits specified in the Auto Alignment interface.

The next stage is the patient re-alignment stage. Patient re-alignment is entered whenever the system encounters a recoverable error (including operator pause), and the system is resumed from this state. Patient re-alignment is handled the same way as patient alignment. In other words, after the initial acquisition, further adjustments can be done automatically using the "AUTO ALIGN" button in the Couch Adjustment interface.

The final stage is the treatment delivery stage. Treatment delivery is initiated when the corrective motions for the table fall below pre-specified limits for translations and rotations. The limit for patient yaw is larger than those for other rotations, and are corrected by the robot. The corrective motions downloaded to the robot includes translations and the specified set of rotations. The robot moves to the nominal position for the node, correct by the specified translation and rotation, and then enable the x-ray beam generator. At the end of dose delivery for the node, the robot returns to the nominal position, (i.e. zero rotations and translations), and proceed to the next node in this nominal position.

The controller includes software for error detection, reporting, and correction. In one embodiment, the error handling software includes "operator pause" functionality. This functionality allows the user to stop image acquisition, if one is in progress, and return to a target alignment or realignment mode. The user can also stop the table motion, if one is in progress, and return to the target alignment/realignment mode. The user can also stop subsequent image acquisitions and table motions, if the "auto alignment" mode is in progress.

In one embodiment, the error handling software also includes a functionality for handling TLS (target locating system) errors. Appropriate TLS errors, such as soft algorithm errors, and/or E-stop for hardware errors, are reported. Upon acknowledgement of the error, the controller can return to the alignment or re-alignment state. The user can stop subsequent image acquisitions and table motions, if "auto alignment" is in progress. During the initial alignment, the "patient out of bounds" error is disabled, but the "TREAT" button is disabled until the patient is within bounds.

In one embodiment, the error handling software includes a functionality for handling table interface errors. Table interface errors such as communication errors are handled as soft errors, which require user acknowledgment, but do not engage an E-stop. In one embodiment, the error handling software includes a functionality for handling E-stop. In this embodiment, an E-stop stops computer controlled table motion, using a dual redundant mechanism. The controller software stops generating any further motion command signals. The table controller hardware is disabled from table movement when an E-stop is engaged. Even when the E-stop is engaged, the table is capable of moving using the handheld user interface unit. On resumption from pause or a recoverable E-stop, the E-stop is cleared by system reset from the operator console, which then goes into a patient re-alignment state. At this stage, the user can use auto-align to refine the patient position. The RESUME button on the patient re-alignment screen enables resumption of treatment delivery.

Many other embodiments are possible. For example, the patient positioning assembly described above can be used with therapeutic radiation systems other than Cyberknife. The controller software may include functionalities other than those described above.

Other embodiments are within the following claims.

What is claimed is:

1. A patient positioning assembly for adjusting a patient position during radiosurgery, said patient positioning assembly comprising:
   a. a support device to support the patient during treatment; and
   b. a controller coupled to the support device to control the motion of said support device, said controller comprising:
      i) means for receiving pre-treatment scan data representative of one or more pre-treatment scans of a treatment target within the patient, the pre-treatment scans showing the position and orientation of said target with respect to a pre-treatment coordinate system;
      ii) means for receiving image data containing information regarding the near real time position and orientation of said target with respect to a treatment coordinate system, said treatment coordinate system having a predetermined relationship to said pre-treatment coordinate system; and
      iii) means, responsive to said pre-treatment scan data and said image data, for generating at least one motion command signal for implementing one or more corrective motions of said support device to substantially match the position and orientation of said target as shown in said pre-treatment scan data of said target with the position and orientation of said target of the near real time image data.

2. A patient positioning assembly in accordance with claim 1, wherein said controller includes user interface means for enabling a user to interactively control said corrective motions of the support device, by implementing one or more user-selectable functions.

3. A patient positioning assembly in accordance with claim 2, wherein said user interface means comprises a remote control module that provides the user with remote control capabilities for remote control of the motion of said support device.

4. A patient positioning assembly in accordance with claim 3, wherein said remote control module comprises a handheld pendant.

5. A patient positioning assembly in accordance with claim 2, wherein said user interface means comprises one or more button icons respectively associated with said one or more user selectable functions, and wherein said user selectable functions comprise at least one of:
   a. a function for allowing the user to activate said imaging system so as to initiate the acquisition of one or more near real time images of said target;
   b. a function for allowing the user to move the support device to at least one of:
      i) a first pre-programmed position corresponding to a mounting position for facilitating the mounting of said patient onto said support device;
      ii) a second pre-programmed position corresponding to a nominal treatment position;
   c. a function for displaying to the user a sequence of translations and rotations corresponding to said one or more corrective motions implemented by said motion command signal; and
   d. a function for allowing the user to modify said sequence of translations and rotations.

6. A patient positioning assembly in accordance with claim 5, wherein said user selectable functions further comprise:
   i) a function for allowing the user to compare said translations and rotations with respective pre-specified limits for each translation and rotation;
   ii) a function for allowing the user to modify one or more of said pre-specified limits; and
   iii) a function for allowing the user to activate said treatment beam generator to initiate treatment delivery, upon verification that said translations and rotations identified by said motion command signal fall below said pre-specified limits.

7. A patient positioning assembly in accordance with claim 5, wherein said sequence of translations and rotations encompass up to six degrees of freedom.

8. A patient positioning assembly in accordance with claim 2, wherein said user interface means comprises at least one user interface screen.

9. A patient positioning assembly in accordance with claim 8, wherein said user interface screen comprises means for allowing the user to adjust one or more imaging parameters of an imaging system.

10. A patient positioning assembly in accordance with claim 9, wherein said imaging parameters comprise at least one of:
    a) an intensity of x-rays in one or more imaging beams generated by said imaging system;
    b) a spectral distribution of said x-rays in said imaging beams;
    c) energy of x-rays in imaging beam;
    d) selection and de-selection of fiducials;
    e) one or more rigid body parameters; and
    f) a number of near real-time images to be acquired.

11. A patient positioning assembly in accordance with claim 1, further comprising at least one sensor for sensing the position and orientation of said support device, and for generating at least one sensor signal representative thereof; and
    means, responsive to said at least one sensor signal, said pre-treatment scan data, and said image data, for generating at least one motion command signal for implementing one or more corrective motions of said support device, and at least one actuator for moving said support device in accordance with said motion command signal from said controller.

12. A patient positioning assembly in accordance with claim 11, further comprising a support device interface module for enabling said support device to interface with said sensor, said controller, said actuator, and said user interface means; said support device interface module includes:
    means for communicating with said sensor, so as to receive from said sensor said sensor signal;
    means for communicating with said controller, so as to provide position feedback to said controller in accordance with said sensor signal, and so as to receive said motion command signal from said controller; and
    means for communicating with said actuator so as to transmit said motion command signal from said remote controller onto said actuator.

13. A patient positioning assembly in accordance with claim 11, wherein said controller further comprises: means for detecting one or more errors, means for reporting one or more errors, and means for correcting one or more errors.

14. A patient positioning assembly in accordance with claim 13, wherein said one or more errors comprise at least one of:
  a) a communication error between said controller and one of said sensor, said support device, and said actuator;
  b) an error in said information regarding target position and orientation;
  c) an error said corrective motions; and
  d) an interface error between said support device and at least one of said sensor, said controller, and said actuator.

15. A patient positioning assembly in accordance with claim 13, wherein said means for correcting one or more errors comprises at least one of:
  a. means for deactivating an imaging system so as to prevent any further images from being acquired;
  b. means for preventing any further corrective motion of said supporting device;
  c. lockout means for turning off, during an error correction process, any and all radiation and motion from any and all components of the patient positioning system.

16. A patient positioning assembly in accordance with claim 1, wherein said one or more corrective motions of said support device have at least three degrees of freedom.

17. A patient positioning assembly in accordance with claim 1, wherein said one or more corrective motions of said support device have at least five degrees of freedom.

18. A patient positioning assembly in accordance with claim 17, wherein said five degrees of freedom comprise three translational degrees of freedom for translations along mutually orthogonal x-, y-, and z-coordinate axes, and two rotational degrees of freedom for roll- and pitch-rotations around roll- and pitch-axes, respectively.

19. A patient positioning assembly in accordance with claim 17, wherein said controller further comprises means for converting said information regarding near real time target position and orientation into one or more units of motion of said support device in at least one of said five degrees of freedom.

20. A patient positioning assembly in accordance with claim 17, further comprising an external device for correcting for a sixth degree of freedom of said corrective motions of said support device, wherein said sixth degree of freedom is a rotational degree of freedom for yaw-rotation about a yaw-axis.

21. A patient positioning assembly in accordance with claim 17, wherein said external device comprises a robot.

22. A patient positioning assembly in accordance with claim 1, wherein said support device comprises a table.

23. A patient positioning assembly in accordance with claim 1, wherein said controller has pre-programmed therein at least a first and a second position of said support device.

24. A patient positioning assembly in accordance with claim 23, wherein said first pre-programmed position of said support device corresponds to a mounting position for facilitating the mounting of said patient onto said support device.

25. A patient positioning assembly in accordance with claim 23, wherein said second pre-programmed position of said support device corresponds to a nominal treatment position in which said patient was treated at a time period prior to a current treatment.

26. A patient positioning assembly in accordance with claim 1, wherein said pre-treatment scan data comprise 3D scan data.

27. A patient positioning assembly in accordance with claim 1, wherein said pre-treatment scan data comprise at least one of: CT scan data, PET scan data, MRI scan data, or ultrasound scan data.

28. A patient positioning assembly comprising:
  A. a support device to support a patient during treatment; and
  B. a controller coupled to the support device, said controller comprising:
    a) an input module to receive pre-treatment scan data and near real time image data of a target;
    b) a comparator to determine one or more corrective motions of said support device from the pre-treatment scan data and near real time image data; and
    c) a signal generator coupled to said comparator for generating at least one motion command signal to implement one or more corrective motions of said support device.

29. A patient positioning assembly in accordance with claim 28, wherein said controller further comprises user interface to enable the user to interactively control a motion of the support device by implementing one or more user-selectable functions.

30. A patient positioning assembly in accordance with claim 28, wherein the controller controls a motion of the support device to align the target with respect to a radiosurgical treatment apparatus.

31. A patient positioning assembly in accordance with claim 30, wherein the pre-treatment scan data is representative of pre-treatment scans of the target showing the position and orientation of said target with respect to a pre-treatment coordinate system, and wherein the near real time image data comprises information regarding the near real time position and orientation of said target with respect to a treatment coordinate system, said treatment coordinate system having a predetermined relationship to said pre-treatment coordinate system.

32. A patient positioning assembly in accordance with claim 31, wherein the radiosurgical treatment apparatus comprises:
  a. an imaging system for generating the near real time image data;
  b. a robot including an articulated arm assembly; and
  c. an x-ray source mounted at a distal end of said arm assembly to selectively emit an x-ray beam.

33. A patient positioning assembly in accordance with claim 31, wherein the controller compensates for one or more motions of said x-ray source implemented by said robot to cause a desired x-ray radiation pattern to be delivered to said target throughout treatment.

34. A patient positioning assembly in accordance with claim 31, wherein said corrective motions of said support device, implemented by said motion command signal generated by said controller, compensate for one or more motions of said x-ray source implemented by said robot to maximize a workspace available to said treatment apparatus.

35. A patient positioning assembly in accordance with claim 31 wherein said corrective motions of said support device, implemented by said motion command signal generated by said controller, compensate for one or more patient motions of said patient that take place during treatment.

36. A patient positioning assembly in accordance with claim 35, wherein said one or more patient motions comprise at least one of:
  a. a respiratory motion of said patient;
  b. a muscular shifting of one or more members of said patient;

c. motion caused by one of sneezing, coughing, and hiccuping of said patient; and
d. cardiac pumping motion of the heart of the patient.

37. A patient positioning assembly in accordance with claim 31, wherein the radiosurgical treatment apparatus is an x-ray source mounted at a distal end of an articulated arm assembly of a robot-based frameless stereotactic radiosurgery system.

38. A method, comprising:
receiving pre-treatment scan data representative of one or more pre-treatment scans of a treatment target within a patient on a support device, the pre-treatment scans showing the position and orientation of the treatment target with respect to a pre-treatment coordinate system;
receiving image data containing information regarding the near real time position and orientation of the treatment target with respect to a treatment coordinate system, the treatment coordinate system having a pre-determined relationship to the pre-treatment coordinate system; and
generating at least one motion command signal for implementing one or more corrective motions of the support device to move the support device to substantially match the position and orientation of said target as shown in said pre-treatment scan data of said target with the position and orientation of said target of the near real time image data.

39. The method of claim 38, wherein receiving pre-treatment scan data, receiving image data, and generating at least one motion command signal are performed using software.

40. The method of claim 38, wherein generating the at least one motion command signal comprises comparing the position and orientation of the treatment target, as shown in the near real-time image data, with the position and orientation of the treatment target as shown in the pre-treatment scan data.

41. The method of claim 40, wherein generating the at least one motion command signal further comprises calculating an amount of translations and rotations required in order for the position and orientation of the treatment target, as shown in the near real time images, to substantially match the position and orientation of the treatment target, as shown in the pre-treatment scans.

42. The method of claim 41, further comprising converting the amount of translations and rotations into one or more units of motion of the support device.

43. The method of claim 42, wherein comparing the position and orientation of the treatment target, calculating the amount of translations and rotations, and converting the amount of translations and rotations into one or more units of motion of the support device are performed using software.

44. The method of claim 42, wherein the one or more units of motion of the support device include at least three degrees of freedom.

45. The method of claim 42, wherein the one or more units of motion of the support device include at least five degrees of freedom.

46. The method of claim 38, further comprising:
providing at least one position sensor coupled to the support device;
determining the position and orientation of the support device using the at least one position sensor; and
generating at least one sensor signal representative thereof from the at least one position sensor.

47. The method of claim 46, wherein generating the at least one motion command signal comprises comparing the position and orientation of the treatment target, as shown in the near real-time image data, with the position and orientation of the treatment target as shown in the pre-treatment scan data, and with the position and orientation, as represented in the at least one sensor signal.

48. The method of claim 38, further comprising providing at least one actuator coupled to the support device, wherein generating at least one motion command signal for implementing one or more corrective motions of the support device to move the support device comprises moving the support device with respect to the treatment apparatus using the at least one actuator.

49. The method of claim 38, further comprising providing an external device coupled to the support device, wherein moving the support device with respect to the treatment apparatus is performed using the external device.

50. The method of claim 49, wherein the external device is a robot.

51. The method of claim 50, wherein the robot includes an articulated arm assembly.

52. The method of claim 38, wherein receiving pre-treatment scan data comprises at least one of computerized tomography (CT), positron emission data (PET) scan data, magnetic resonance imaging (MRI) scan data, or ultrasound scan data.

53. The method of claim 38, further comprising providing a user interface coupled to the support device, the user interface including one or more user-selectable functions.

54. The method of claim 53, wherein the one or more user-selectable functions comprise at least one of:
activating an imaging system so as to initiate the acquisition of one or more near real time images of said target;
adjusting one ore more imaging parameters of the imaging system;
moving the support device to at least one of:
a first pre-programmed position corresponding to a loading/unloading for mounting the patient onto the support device; and
a second pre-programmed position corresponding to a treatment position in which the patient was treated at a time period prior to a current treatment;
displaying to the user a sequence of translations and rotations corresponding to the one or more corrective motions of the support device for moving the support device with respect to the treatment apparatus;
modifying the sequence of translations and rotations;
comparing the translations and rotations with respective pre-specified limits for each translation and rotation;
modifying one or more of said pre-specified limits; and
activating a treatment beam generator of the treatment apparatus to initiate treatment delivery, upon verification that said translations and rotations identified by said motion command signal fall below said prespecified limits.

55. The method of claim 54, wherein the imaging parameters comprise at least one of:
an intensity of x-rays in one or more imaging beams generated by said imaging system;
a spectral distribution of said x-rays in said imaging beams;
energy of x-rays in imaging beam;
selection and de-selection of fiducials;
one or more rigid body parameters; and
a number of near real-time images to be acquired.

56. The method of claim 53, wherein the user interface interactively controls the position and orientation of the support device for substantially aligning the position and orientation of the treatment target as shown in the pre-treatment scan data of the treatment target.

57. A method, comprising:
proving a support device;
providing a therapeutic radiation source;
moving the support device with respect to the therapeutic radiation source in at least 3 degrees of freedom to align a treatment target with respect to the therapeutic radiation source, wherein moving the support device comprises:
determining a position and orientation of the treatment target with respect to a pre-treatment coordinate system;
determining a near real time position and orientation of the treatment target with respect to a treatment coordinate system, the treatment coordinate system having a predetermined relationship to the pre-treatment coordinate system; and
determining one or more corrective motions of the support device to move the support device with respect to the therapeutic radiation source to substantially match the position and orientation of the treatment target as shown in said pre-treatment scan data of said target with the position and orientation of the treatment target of the near real-time image data.

58. The method of claim 57, wherein the therapeutic radiation source is a x-ray linear accelerator ("linac").

59. The method of claim 57, wherein the treatment apparatus is a frameless stereotactic radiosurgery system.

60. The method of claim 57, wherein the treatment apparatus is a gantry-based radiosurgery system.

* * * * *